United States Patent
Joshi

(10) Patent No.: US 9,270,011 B2
(45) Date of Patent: Feb. 23, 2016

(54) ANTENNA COUPLED TO A COVER CLOSING AN OPENING IN AN IMPLANTABLE MEDICAL DEVICE

(71) Applicant: CYBERONICS, INC., Houston, TX (US)

(72) Inventor: Himanshu Joshi, Houston, TX (US)

(73) Assignee: CYBERONICS, INC., Houston, TX (US)

( * ) Notice: Subject to any disclaimer, the term of this patent is extended or adjusted under 35 U.S.C. 154(b) by 349 days.

(21) Appl. No.: 13/835,036

(22) Filed: Mar. 15, 2013

(65) Prior Publication Data

US 2014/0266921 A1    Sep. 18, 2014

(51) Int. Cl.
*H01Q 1/24*    (2006.01)
*H01Q 13/10*   (2006.01)
*A61N 1/372*   (2006.01)

(52) U.S. Cl.
CPC .............. *H01Q 1/24* (2013.01); *A61N 1/37229* (2013.01); *H01Q 13/10* (2013.01)

(58) Field of Classification Search
CPC ......... H01Q 1/24; H01Q 13/10; H01Q 1/088; H01Q 1/2258; H01Q 9/0407; A61N 1/375
USPC ................................ 343/702, 767; 607/36, 37
See application file for complete search history.

(56) References Cited

U.S. PATENT DOCUMENTS

| | | | |
|---|---|---|---|
| 6,670,926 B2 * | 12/2003 | Miyasaka ...................... | 343/702 |
| 2005/0222633 A1 | 10/2005 | Edvardsson | |
| 2006/0028784 A1 | 2/2006 | Brendel | |
| 2008/0033500 A1 | 2/2008 | Strother et al. | |
| 2009/0248112 A1 | 10/2009 | Mumbru et al. | |
| 2010/0060431 A1 | 3/2010 | Stevenson et al. | |
| 2010/0114205 A1 | 5/2010 | Donofrio et al. | |
| 2010/0161002 A1 * | 6/2010 | Aghassian et al. .............. | 607/60 |
| 2010/0168818 A1 | 7/2010 | Barror et al. | |
| 2010/0194541 A1 | 8/2010 | Stevenson et al. | |
| 2010/0321163 A1 | 12/2010 | Stevenson | |
| 2011/0004076 A1 | 1/2011 | Janna et al. | |
| 2011/0134013 A1 * | 6/2011 | Rawat et al. ................... | 343/873 |
| 2012/0276854 A1 * | 11/2012 | Joshi et al. ...................... | 455/73 |
| 2012/0276856 A1 | 11/2012 | Joshi et al. | |

OTHER PUBLICATIONS

International Application No. PCT/US2014/032174, "PCT Search Report and Written Opinion," dated Aug. 21, 2014, 13 pages.

* cited by examiner

*Primary Examiner* — Hoang V Nguyen

(57) ABSTRACT

An implantable medical device includes a housing. An opening is present in the housing. The implantable medical device includes communication circuitry in the housing. The implantable medical device includes a cover coupled to edges of the housing defining the opening to substantially close the opening. The implantable medical device also includes an antenna coupled to the cover. The antenna is electrically coupled to the communication circuitry.

22 Claims, 4 Drawing Sheets

ANTENNA COUPLED TO A COVER CLOSING AN OPENING IN AN IMPLANTABLE MEDICAL DEVICE

FIELD OF THE DISCLOSURE

The present disclosure is generally related to an antenna for an implantable medical device.

BACKGROUND

An implantable medical device (IMD) in a patient may wirelessly communicate with an external device. Wireless communication for IMDs may be at MICS radio frequencies (i.e., medical implant communications service radio frequencies between 402 MHz and 405 MHz), at ISM radio frequencies (i.e., industrial, scientific, and medical radio frequencies), or at other radio frequencies. The IMD may be a nerve stimulator (e.g., a vagus nerve stimulator), a pacemaker or other heart stimulation device, or another type of medical device. Wireless communication may enable the IMD to receive parameters, instructions, data, or combinations thereof, that specify operating characteristics of the IMD. Wireless communication may also enable the IMD to send information to the external device. The information may include operating parameters of the IMD, operation data, physiological data associated with the patient, power source information, and other data.

Wireless communication with an IMD can be problematic. For example, when the IMD has a conductive housing, and a communication antenna is located within the conductive housing, signals may be blocked or attenuated by the housing.

SUMMARY

In a particular embodiment, an implantable medical device includes a housing. An opening is present in the housing. The implantable medical device includes communication circuitry in the housing. The implantable medical device includes a cover coupled to edges of the housing defining the opening to substantially close the opening. The implantable medical device also includes an antenna coupled to the cover. The antenna is electrically coupled to the communication circuitry.

In another particular embodiment, an implantable medical device includes a housing. An opening is present in the housing. The implantable medical device includes communication circuitry in the housing. The implantable medical device includes a cover coupled to edges of the housing defining the opening to substantially close the opening. The implantable medical device includes a slot antenna coupled to the cover. The slot antenna includes a first conductive region proximate to a first side of a slot and a second conductive region proximate to a second side of the slot. The implantable medical device includes a feed feedthrough electrically coupled to the slot antenna adjacent to the slot in the first conductive region and electrically coupled to the communication circuitry. The implantable medical device also includes one or more ground feedthroughs electrically coupled to the slot antenna adjacent to the slot in the second conductive region and electrically coupled to the communication circuitry.

In another particular embodiment, an implantable medical device includes a housing. An opening is present in the housing. The implantable medical device includes a circuit board in the housing. At least a portion of the circuit board is located below the opening. The circuit board includes a first antenna where at least a portion of the first antenna is located below the opening. The implantable medical device includes a cover coupled to edges of the housing defining the opening to substantially close the opening. The cover enables passage of radio frequency signals at one or more communication frequencies to and from the first antenna. The implantable medical device also includes a second antenna coupled to the cover and electrically coupled to the circuit board.

DETAILED DESCRIPTION

Figure 1:
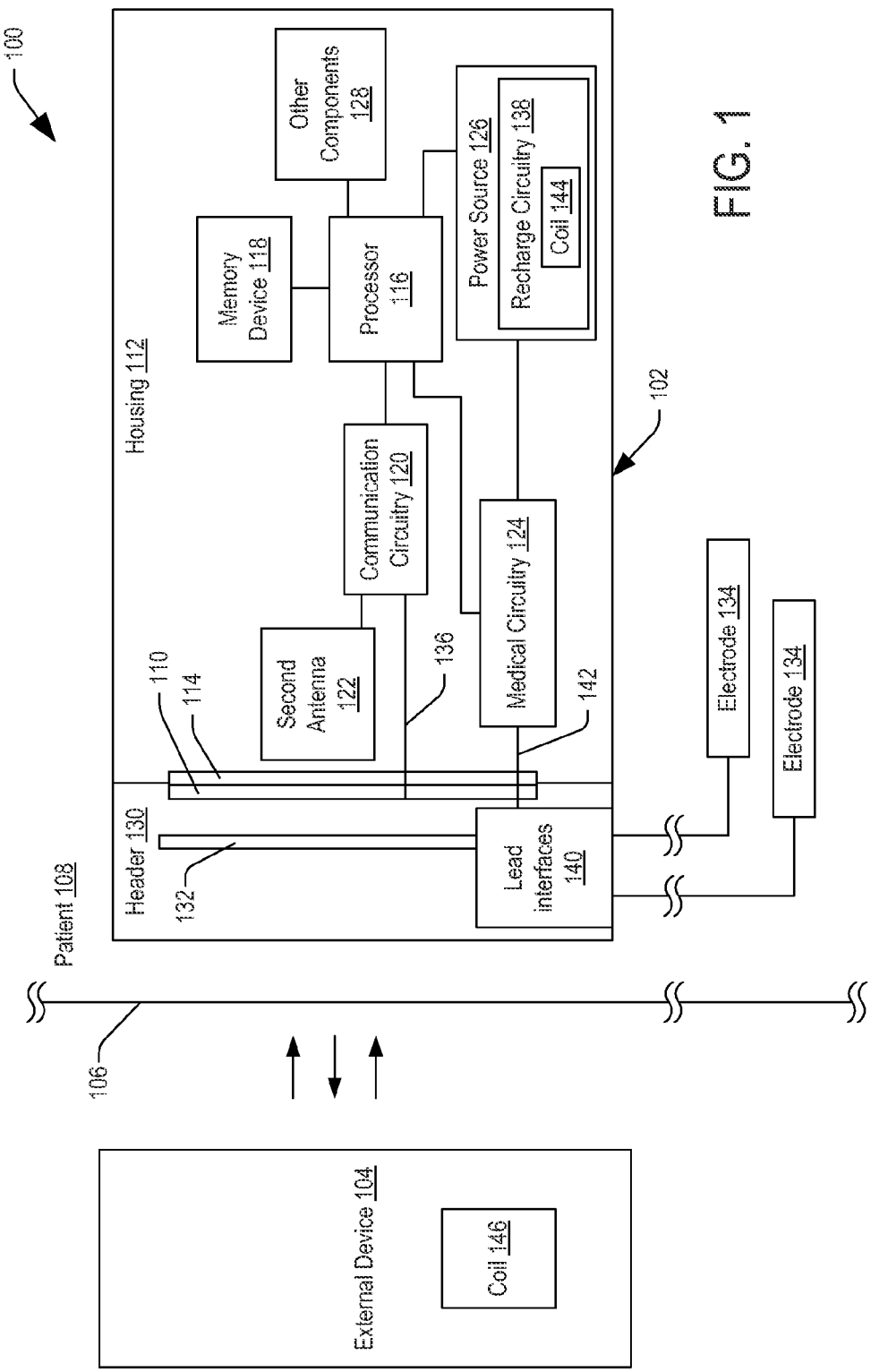
FIG. 1 is a block diagram of a first embodiment of a system that includes an implantable medical device and an external charging device.

FIG. 1 is a block diagram of a particular embodiment of a system 100 that includes an implantable medical device (IMD) 102 and an external device 104. The IMD 102 may be positioned beneath skin 106 of a patient 108. The IMD 102 may receive first signals at one or more communication frequencies from the external device 104 via a first antenna 110, may transmit second signals at one or more communication frequencies to the external device 104 via the first antenna 110, or both. The first antenna 110 may be a slot antenna positioned external to a housing 112 of the IMD 102. The first antenna 110 may be coupled to a cover 114 that closes an opening in the housing 112. The IMD 102 may receive sensor data from one or more sensors coupled to the IMD 102. The IMD 102 may also provide treatment signals to the patient 108 at scheduled times, may provide treatment signals to the patient 108 based on the sensor data, or both.

The IMD 102 may include the housing 112, components 116-128 within the housing 112, the cover 114, a header 130, an antenna shield 132, the first antenna 110, or a combination thereof. The housing 112 may be a metallic housing made of, for example, titanium, a titanium alloy, or another biocompatible metal. The housing 112 may be assembled from two or more pieces. For example, the housing 112 may be formed from a bottom piece and a top piece that are joined together. The pieces of the housing 112 may be joined together by one or more welds, by one or more press fit connections, by fasteners (e.g., screws, rivets, snaps, etc.), by adhesive, by other connection systems, or by combinations thereof. Components 116-128 of the IMD 102 may be positioned in the housing 112 before the pieces of the housing 112 are joined together.

The components 116-128 of the IMD 102 may include, but are not limited to, a processor 116, a memory device 118, communication circuitry 120, a second antenna 122, medical"

circuitry 124, a power source 126, other components 128, or a combination thereof. Some or all of the components 116-128 may be positioned on, or may be part of, one or more circuit boards coupled to the housing 112. The components 116-128 may be hermetically sealed within the housing 112 when the IMD 102 is assembled.

The processor 116 may control operation of the IMD 102. The processor 116 may be communicatively coupled to the memory device 118. The memory device 118 may include one or more devices and may include internal memory of the processor 116. The memory device 118 may include (e.g. store) instructions executable by the processor 116 to implement functionality of the IMD 102. The memory device 118 may store parameters and data used by the processor 116 to determine characteristics (e.g., amplitude, polarity, frequency, pulse width, pulse period, duty cycle, charge balancing, signal duration, etc.) of treatment signals to be applied to the patient 108 by the IMD 102. The parameters and data may also indicate when the treatment signals are to be applied to the patient 108 via one or more electrodes 134 (e.g., at scheduled times or in response to one or more conditions). The memory device 118 may also, or in the alternative, store data identifying applied treatment signals, diagnostic information associated with the IMD 102, and sensor data from one or more sensors coupled to the IMD 102. The data may be received from one or more of the electrodes 134, from one or more heart beat sensors, from one or more temperature sensors, from other sensors, or combinations thereof. For example, the electrodes or one or more sensors may be implanted within or coupled to tissue of the patient 108 and may transmit data, or signals, to the IMD 102 via wired or wireless connections.

The processor 116 may be coupled to the communication circuitry 120. The communication circuitry 120 may be coupled to the first antenna 110 and the second antenna 122. The second antenna 122 may be a dipole antenna, monopole antenna, a serpentine antenna, a slot antenna, a patch antenna, plane-inverted-F antenna, helical antenna, a fractal antenna, a loop antenna, or an antenna with another form factor positioned within the housing 112. In some embodiments, the IMD 102 may not include the second antenna 122 and the first antenna 110 may be coupled by feedthroughs 136 to a ground and a feed line of the communication circuitry 120. The communication circuitry 120 may include matching components to improve performance of the first antenna 110, the second antenna 122, or both, at communication frequencies used by the IMD 102 to transmit and receive data via the antennas 110, 122.

The communication circuitry 120 may enable the processor 116 to wirelessly send information via one or more of the antennas 110, 122 to the external device 104. The information may include data stored by the memory device 118. For example, the information may include data corresponding to operation of the IMD 102, diagnostic information for the IMD 102, data corresponding to current conditions of the IMD 102, or combinations thereof. The communication circuitry 120 may also, or in the alternative, enable the processor 116 to receive, via one or more of the antennas 110, 122, parameters, data, instructions, or combinations thereof, from the external device 104.

The communication circuitry 120 may include wake-up circuitry. The wake-up circuitry may include matching components to improve performance of the first antenna 110, the second antenna 122, or both, at wake-up signal frequencies. The wake-up signal frequencies may be different than communication frequencies used to transmit and receive data via the antennas 110, 122. For example, in an illustrative embodiment, the wake-up signal frequencies may be at about 2.45 GHz while the communication frequencies used to communicate via the antennas 110, 122 may be at about 400 MHz. The external device 104 may send a wake-up signal to the IMD 102 when a communication session is to be established between the IMD 102 and the external device 104. The wake-up circuitry may send signals received at one or more of the antennas 110, 122 at the wake-up signal frequencies to the processor 116.

When the processor 116 determines that the signals received from the wake-up circuitry include the wake-up signal, the processor 116 may cause the communication circuitry 120, components capable of entering a sleep state (e.g., recharge circuitry 138 of the power source 126), or both, to transition from a sleep state to an active state where the components capable of entering the sleep state are ready to communicate, perform functions, or both. The communication circuitry 120 and the other components of the IMD 102 capable of entering a sleep state may enter the sleep state after particular periods of inactivity, or in response to a received sleep command, to conserve power or for other reasons. In response to receipt of the wake-up signal, the processor 116 may cause the communication circuitry 120 to send an acknowledgement signal to the external device 104 that informs the external device 104 that the IMD 102 is ready to communicate with the external device 104.

The processor 116 may be coupled to the medical circuitry 124. The medical circuitry 124 may be coupled to one or more lead interfaces 140 in the header 130 via feedthroughs 142. The medical circuitry 124 may include therapy circuitry to provide treatment signals to the patient 108 via one or more of the feedthroughs 142. The medical circuitry 124 may also, or in the alternative, include sensing circuitry to receive physiological data associated with the patient 108 from one or more sensors coupled to the IMD 102. The one or more sensors may include, but are not limited to, one or more of the electrodes 134, one or more temperature sensors, a heart rate sensor, an oximeter, an accelerometer, a blood pressure monitor, another type of sensor, or combinations thereof.

The processor 116 may be coupled to the power source 126. The power source 126 may also be coupled to one or more of the memory device 118, the communication circuitry 120, the medical circuitry 124, and the other components 128. The power source 126 may include one or more batteries, capacitors, other charge storage devices, or combinations thereof, to power the IMD 102 and components thereof. Batteries of the power source 126 may include rechargeable batteries, non-rechargeable batteries, or combinations thereof. The power source 126 may include or be coupled to the recharge circuitry 138 that enables the power source 126 to be recharged. In an embodiment, the recharge circuitry 138 may include a coil 144. A current may be induced in the coil 144 by a primary current flowing through a coil 146 of the external device 104. The induced current in the coil 144 may be used to recharge the power source 126.

The processor 116 may receive status information from the recharge circuitry 138 during recharging of the power source 126. The status information may include charge frequency information to facilitate determination of a resonant frequency for charging, charge completion information, other information, or combinations thereof. The external device 104 may receive charge information from the processor 116 via the communication circuitry 120 and one or more of the antennas 110, 122. The charge information may include status information received by the processor 116 from the recharge circuitry 138, information determined by the processor 116 based on the status information, information received from the other components 128 (e.g., temperature information of the power source 126, the housing 112, or both), commands (e.g., a reduce recharge rate command, a stop recharge command, etc.), or combinations thereof. The commands may be sent based on status of a recharge process. For example, the reduce recharge rate command may be sent when a temperature increase rate of the IMD 102 exceeds a threshold. In response to the reduce recharge rate command, the external device 104 may adjust one or more properties of a charging signal applied to the coil 146 or may initiate periodic charging of the power source 126 followed by periods of time when no charging occurs until the power source 126 is recharged to a threshold state. As another example, the stop recharge command may be sent to the external device 104 when the power source 126 is recharged to the threshold state. In response to the stop recharge command, the external device 104 may cease applying the charging signal to the coil 146.

The processor 116, the components 116-128 of the IMD 102, and the housing 112 may be coupled to one or more of the other components 128. The other components 128 may include but are not limited to temperature sensors, other sensors, flexible electrical connectors, mounts, and so forth.

The housing 112 may have an opening that is closed, or otherwise filled by the cover 114. The cover 114 may be coupled to the housing 112 to substantially close the opening. The cover 114 may be part of one or more feedthroughs and may provide openings for one or more conductors of the one or more feedthroughs to pass through. The cover 114 may be sealed to the housing and the conductors passing through the openings in the cover 114 may be sealed during, or prior to, hermetical sealing of the housing 112 of the IMD 102. First openings for feedthroughs 142 may pass through the cover 114 and the first antenna 110. Second openings for feedthroughs 136 may pass through the cover 114 and the first antenna 110. The cover 114 may be a dielectric material (e.g., a ceramic, a polymer, or other dielectric material). The cover 114 may facilitate passage of radio frequency signals to and from the second antenna 122.

The feedthroughs 142 may pass from the medical circuitry 124 in the housing 112 through one or more openings in the cover 114 and the first antenna 110 to one or more lead interfaces 140 in the header 130. The feedthroughs 142 may be sealed to the cover 114 and electrically insulated from the first antenna 110. In an embodiment, the feedthroughs 142 for a particular lead interface of the lead interfaces 140 may include a feed and a return. In another embodiment, a particular lead interface may be connected to a single feedthrough 142. The single feedthrough 142 may be a feed for a treatment signal. A return path for the treatment signal may be through the patient 108 to the housing 112.

The feedthroughs 136 may pass from the communication circuitry 120 in the housing 112 through openings in the cover 114 to the first antenna 110. The feedthroughs 136 may be electrically coupled to the first antenna 110. The feedthroughs 136 may include at least one feed feedthrough and one or more ground feedthroughs. In some embodiments, the feedthroughs 136 may also be electrically coupled to the second antenna 122.

The header 130 may be coupled to the housing 112. The header 130 may be formed of one or more biocompatible polymers. The header 130 may be coupled to the housing 112 by a press fit, by one or more connectors (e.g., screws, rivets, snaps, etc.), by an adhesive (e.g., an epoxy), by another type of polymer to metal connection, or by combinations thereof. One or more of the lead interfaces 140 may be positioned in or attached to the header 130. One or more of the electrodes 134, other treatment devices, sensors, or combinations thereof, may be coupled to the lead interfaces 140.

The antenna shield 132 may be attached to or deposited on a bottom surface of the header 130, may be positioned in the header 130, or may be attached to or deposited on a top surface of the header 130. In some embodiments, the IMD 102 may not include the antenna shield 132. The antenna shield 132 may provide radio frequency shielding to the first antenna 110, to the second antenna 122, or both. The radio frequency shielding may reduce passage of at least some (e.g., attenuate) radio frequency signals to and from the antennas 110, 122. For example, the antenna shield 132 may attenuate low frequency signals (e.g., noise) more than higher frequency signals (e.g., signals at one or more communication frequencies) while still having relatively small attenuation at the communication frequencies.

The first antenna 110 may be coupled to the cover 114 closing the opening in the housing 112. The first antenna 110 may be electrically coupled to the communication circuitry by the feedthroughs 136. The first antenna 110 may be a slot antenna. The first antenna 110 may be electrically coupled (e.g., brazed) to the housing 112 to form an electrical connection between the housing 112 and the first antenna 110. The electrical connection between the housing 112 and the first antenna 110 may enable surfaces of the housing 112 that define the opening to be radiating/receiving elements of the first antenna 110 in addition to the radiating/receiving elements defined by the slot of the first antenna 110 to improve the performance of the first antenna 110.

The external device 104 may communicate with the IMD 102. The external device 104 may provide data to the IMD 102, may receive information from the IMD 102, or both. In some embodiments, the coil 146 of the external device 104 may be used to recharge a power source 126 of the IMD 102. In other embodiments, the external device 104 may not include the coil 146.

Figure 2:
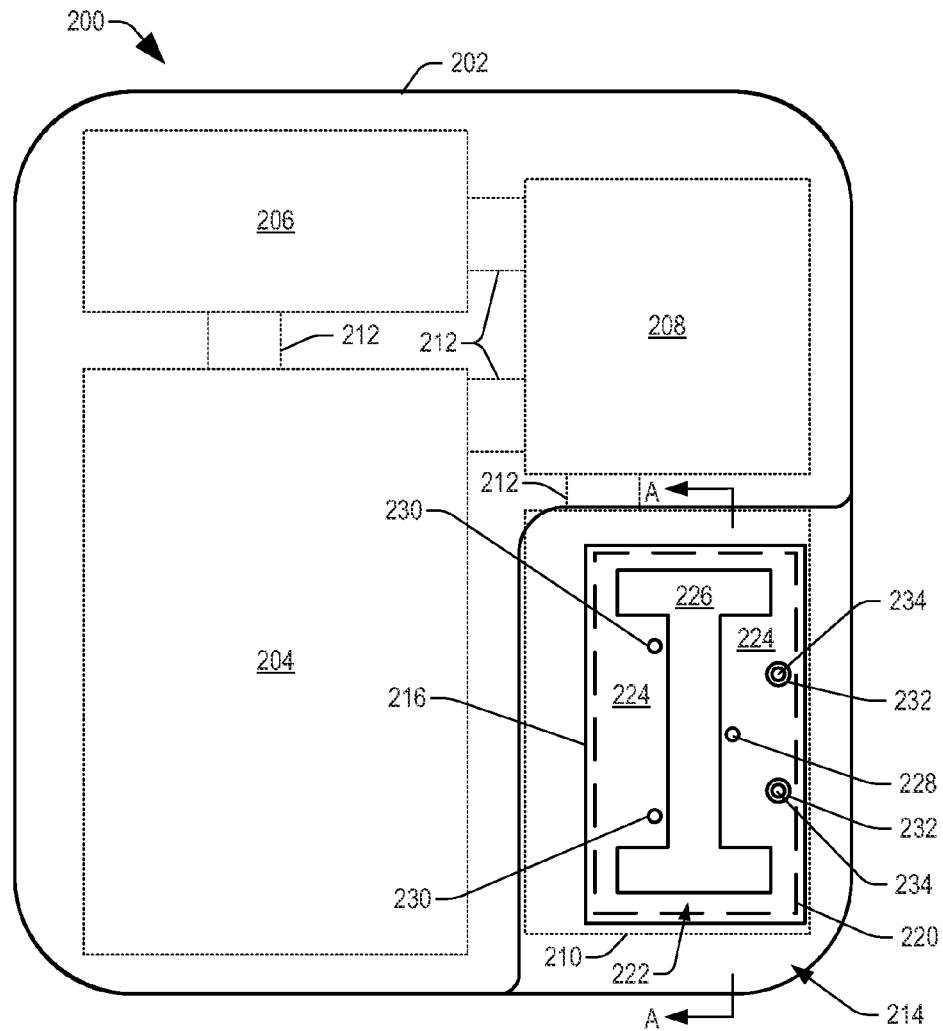
FIG. 2 is a schematic illustration of a top view of a second embodiment of an implantable medical device without a header and lead interfaces.

FIG. 2 is a schematic illustration of a top view of an IMD 200 before a header and lead interfaces are coupled to the IMD 200. In the view depicted in FIG. 2, components 204-212 of the IMD 200 are internally positioned in a housing 202 (as indicated by dotted lines). The components 204-212 may include a power source 204, functional circuitry 206 (e.g., medical circuitry, a processor, a memory device, other components, or combinations thereof), communication circuitry 208, an output circuit board 210, and connectors 212. The communication circuitry 208 may include a receiver, a transmitter, a coder/decoder (CODEC), wake-up circuitry, other components, or combinations thereof, that facilitate communication between an external device (e.g., an external device that is outside of a patient) and the IMD 200 when the IMD 200 is implanted in a patient. The connectors 212 may electrically and communicatively couple the components 204-210 of the IMD 200 to each other.

The housing 202 may include a recessed portion 214. A cover 216 may be coupled to edges of an opening in the recessed portion 214 of the housing 202 to substantially close the opening 220. In FIG. 2, the opening 220 is represented by dashed lines. The cover 216 may include a dielectric material (e.g., a ceramic, a polymer, or other dielectric material).

An antenna 222 may be coupled to the cover 216. The antenna 222 may be a slot antenna that is deposited on the cover 216, printed on the cover 216, adhered to the cover 216, or otherwise coupled to the cover 216. The antenna 222 may include a conductive layer 224, a slot 226, a feed feedthrough 228, and one or more ground feedthroughs 230. FIG. 2 shows two ground feedthroughs as the ground feedthroughs 230, however, one ground feedthrough may be sufficient. In some embodiments, the conductive layer 224 may be electrically coupled to the housing 202. The electrical connection between the housing 202 and the conductive layer 224 may enable the portions of the housing 202 around the opening 220 to be radiating/receiving elements of the antenna 222 to increase performance of the antenna 222. In other embodiments, the conductive layer 224 may not be electrically coupled to the housing 202. The conductive layer 224 may be a metal layer (e.g., a gold layer, a copper layer, or other metallic layer). In other embodiments, the antenna 222 is another type of antenna rather than a slot antenna, such as, but not limited to, a dipole antenna, a monopole antenna, a serpentine antenna, a patch antenna, a plane-inverted-F antenna, a helical antenna, a fractal antenna, a loop antenna, or an antenna with another form factor.

The slot 226 (depicted as an "I" shape in FIG. 2) may be formed by edges of the conductive layer 224. The edges of the conductive layer 224 may form radiating receiving elements of the antenna 222. In other embodiments, a shape of the slot 226 may be different than the "I" shaped slot depicted in FIG. 2. For example, the slot may be a rectangular slot, may be a serpentine slot, may be two or more slots, or may another type of geometrical configuration.

The feed feedthrough 228 may provide signals to the antenna 222 from the communication circuitry 208 when the antenna 222 is used to transmit signals to the external device. The feed feedthrough 228 may be coupled to a feed line in the output circuit board 210. The feed line may be electrically coupled to the communication circuitry 208. The one or more ground feedthroughs 230 may be coupled to a ground for the communication circuitry 208. The ground for the communication circuitry 208 may be a ground plane. The ground plane may be a metal layer of the output circuit board 210 below the opening 220 that is electrically coupled to the communication circuitry 208.

The one or more ground feedthroughs 230 may be positioned relative to the feed feedthrough 228 to promote current flow associated with radio frequency signals at one or more communication frequencies along the edges of the conductive layer 224 that define the slot 226. For example, the feed feedthrough 228 may be positioned on a first side of the slot 226 in the conductive layer 224 close to the slot 226 and on, or near, a center line of the slot 226. The one or more ground feedthroughs 230 may be positioned on an opposite side of the slot 226 in the conductive layer 224 close to the slot 226 and offset a distance from the center line. Additional feed feedthroughs 228 and additional ground feedthroughs 230 may be utilized.

Openings 232 may extend through the cover 216 and the antenna 222. Lead interface feedthroughs 234 that extend from the output circuit board 210 may pass through the openings 232. Electrically insulating sealant may be placed in the openings 232 to isolate the lead interface feedthroughs 234 from the antenna 222 and to form a portion of a hermetic seal for the housing 202 of the IMD 200.

Figure 3:
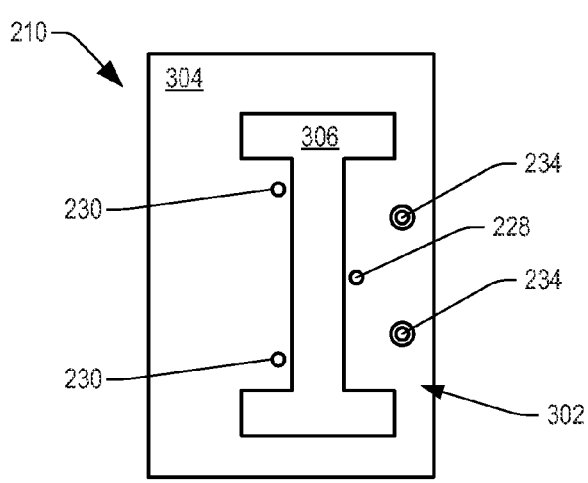
FIG. 3 is a top view of an embodiment of an output circuit board of the implantable medical device depicted in FIG. 2 when the output circuit board includes a slot antenna.

FIG. 3 depicts a top view of an embodiment of the output circuit board 210 shown in FIG. 2 when the output circuit board 210 includes a slot antenna 302. In other embodiments, the output circuit board may include a different type of antenna than the slot antenna 302, or the output circuit board 210 may not include an antenna. The output circuit board 210 may include a conductive layer 304 (e.g., a copper layer) and one or more non-conductive layers 306. The one or more non-conductive layers 306 may be dielectric material of the output circuit board 210. The one or more non-conductive layers 306 may be the same size, or a different size, than the slot 226 of the antenna 222 coupled to the cover 216 (depicted in FIG. 2). The conductive layer 304 may be a ground plane of the output circuit board 210. The conductive layer 304 may be spaced away from the antenna 222 coupled to the cover 216 (depicted in FIG. 2) a sufficient distance to inhibit capacitive coupling between the conductive layer 304 and the antenna 222.

The output circuit board 210 shown in FIG. 3 may include the feed feedthrough 228. The feed feedthrough 228 may be coupled to a feed line on a lower layer of the output circuit board 210. The feed feedthrough 228 may be coupled to, or isolated from, the conductive layer 304. The feed feedthrough 228 may extend from the output circuit board 210 and may be electrically coupled to the conductive layer 224 of the antenna 222 depicted in FIG. 2. The feed feedthrough 228 may be positioned on, or through, the conductive layer 304 on a first side of the one or more non-conductive layers 306 near an edge of the one or more non-conductive layers 306. The feed feedthrough 228 may be positioned to promote current flow associated with radio frequency signals at one or more communication frequencies to radiating/receiving elements of the antenna 302 defined by edges of the conductive layer 304 adjacent to the one or more non-conductive layers 306.

The output circuit board 210 shown in FIG. 3 may include the ground feedthroughs 230. The ground feedthroughs 230 may be coupled to the conductive layer 304. The ground feedthroughs 230 may extend from the conductive layer 304 of the output circuit board 210 and may be electrically coupled to the conductive layer 224 of the antenna 222 depicted in FIG. 2. The ground feedthroughs 230 may be positioned in the conductive layer 304 near an edge of the one or more non-conductive layers 306 on a second side of the one or more non-conductive layers 306 relative to the first side. The ground feedthroughs 230 may be positioned to promote current flow associated with radio frequency signals at one or more communication frequencies to radiating/receiving elements of the antenna 302 defined by edges of the conductive layer 304 adjacent to the one or more non-conductive layers 306.

The output circuit board 210 may also include lead interface feedthroughs 234 that extend out of the output circuit board 210. The lead interface feedthroughs 234 may be electrically isolated from the conductive layer 304.

Figure 4:
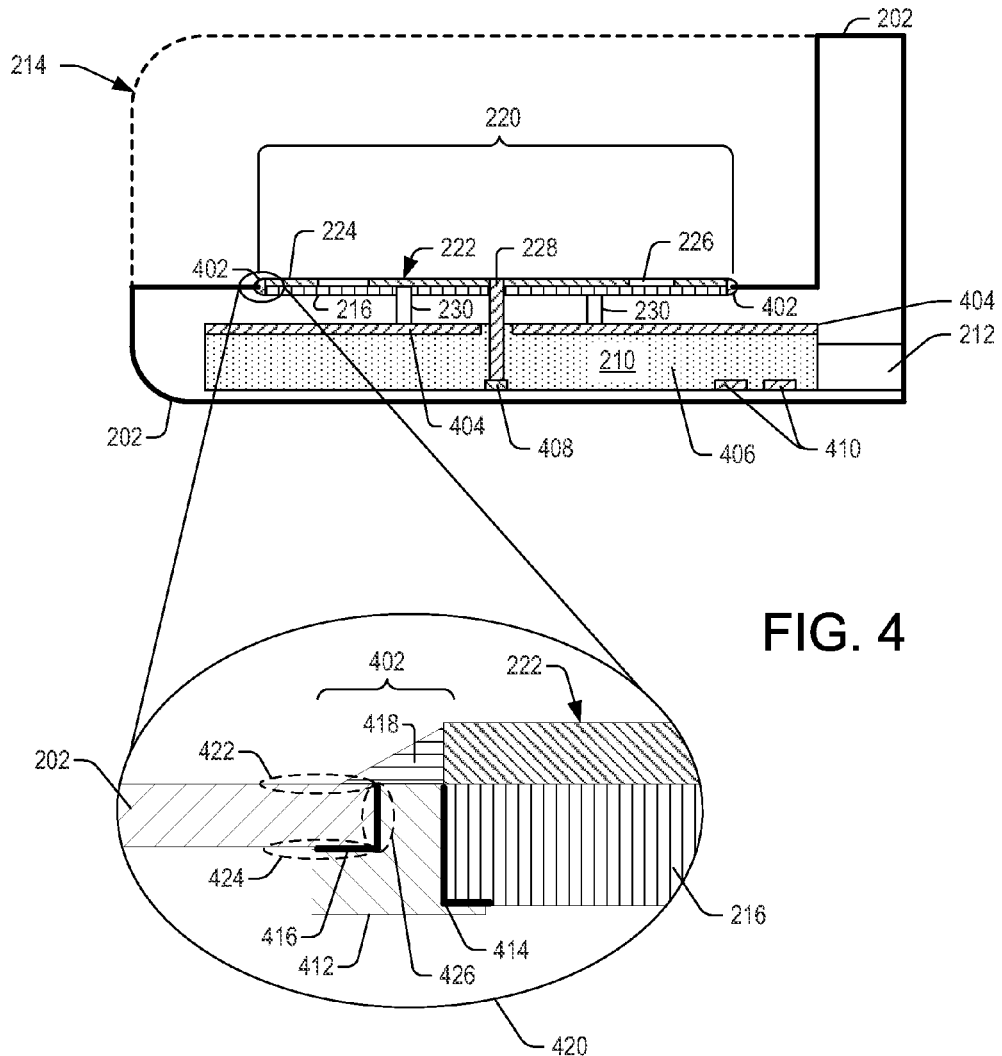
FIG. 4 depicts a cross-sectional view of an embodiment of an implantable medical device taken substantially along a cutting plane indicated by section lines A-A of FIG. 2 when an outboard circuit board of the implantable medical device does not include an antenna.

FIG. 4 depicts a cross-sectional view of the IMD 200 taken substantially along a cutting plane indicated by section lines A-A shown in FIG. 2 when the output circuit board 210 does not include an antenna (i.e., does not include the antenna 302 of FIG. 3). The output circuit board 210 may be positioned in the housing 202 below the opening 220 in the housing 202. The cover 216, with the antenna 222 coupled to the cover 216, may be secured to the housing 202 in the recessed portion 214 of the housing 202 by an electrically conductive seal 402 (e.g., a brazing material or a welding material). The electrically conductive seal 402 may seal the opening 220 and provide an electrical connection between the antenna 222 and the housing 202. The cover 216, the antenna 222, and the electrically conductive seal 402 may be made of biocompatible materials or may be coated with biocompatible materials to inhibit interaction with a patient in the event of failure of a header that is secured to the housing 202 in the recessed portion 214, or in the event of a failure of a connection between the header and the housing 202.

In some embodiments, as illustrated in an exploded view 420, the electrically conductive seal 402 may include a metal flange 412 brazed or otherwise attached to the outer perimeter of the cover 216. A first filler material 414 may be used to attach/seal the metal flange 412 to the cover 216. The cover 216 may be a ceramic based material, the metal flange 412 may include titanium, and the first filler material 414 may include gold. Various other materials may be used to provide a dielectric cover with a flange. The antenna 222 may be deposited on the cover 216. The conductive material for the antenna 222 may include gold and may be a very thin layer (the layers of FIG. 4 are draw for illustrative purposes and may not be to scale). For example, the thickness of the antenna 222 may be on the order of several to hundreds of microns. In some embodiments, the antenna 222 may have a thickness of 2-20 microns. The metal flange 412 may be configured to engage, and be sealed to, edges of the housing 202 defining the opening 220. The edges of the housing 202 around the opening 220 may include a top surface edge 422, a bottom surface edge 424, an inner perimeter surface edge 426, or any combination thereof. In some embodiments, the metal flange 412 may engage the bottom surface edge 424 and the inner perimeter surface edge 426 of the opening 220. The metal flange 412 may be laser welded, brazed, or otherwise sealed to the edges of the housing 202 as illustrated by a joint 416 formed between the housing 202 and the metal flange 412. Positioning the cover 216 so that the metal flange 412 engages the bottom surface edge 424 and the inner perimeter surface edge 426 of the opening 220, as illustrate in the exploded view 420, may allow the cover 216 to be substantially flush with the outside of the housing 202 in the recessed portion 214. A conductive material 418 may be provided to electrically connect the conductive portion of the antenna 222 to the housing 202. The conductive material 418 may be deposited, printed, pressed, brazed, welded, or otherwise attached to the antenna 222 and the housing 202 and may include copper, gold, or some other electrically conductive material.

The output circuit board 210 may include a conductive layer 404, a non-conductive layer 406, a feed line 408 for the antenna 222, and one or more lead interface feedthrough feed lines 410. The feed feedthrough 228 may be electrically coupled to the feed line 408, may pass through the cover 216, and may be electrically coupled to the conductive layer 224 of the antenna 222 on the first side of the slot 226. The one or more ground feedthroughs 230 may be electrically coupled to the conductive layer 404, may pass through the cover 216, and may be electrically coupled to the conductive layer 224 of the antenna 222 on the second side of the slot 226. The conductive layer 404 and the feed line 408 may be electrically coupled by the connector 212 to the communication circuitry 208 (shown in FIG. 2). The one or more lead interface feedthrough feed lines 410 may be coupled by the connector 212 to functional circuitry 206 (shown in FIG. 2). The conductive layer 404 may be spaced a sufficient distance away from the conductive layer 224 of the antenna 222 to inhibit capacitive coupling between the conductive layer 404 and the conductive layer 224. FIG. 4 shows the antenna 222 above or on top of the cover 216, however, in some embodiments, the antenna 222 may be positioned below, or underneath, the cover 216 such that the antenna 222 is closer to the output circuit board 210 and sealed within the housing 202.

Figure 5:
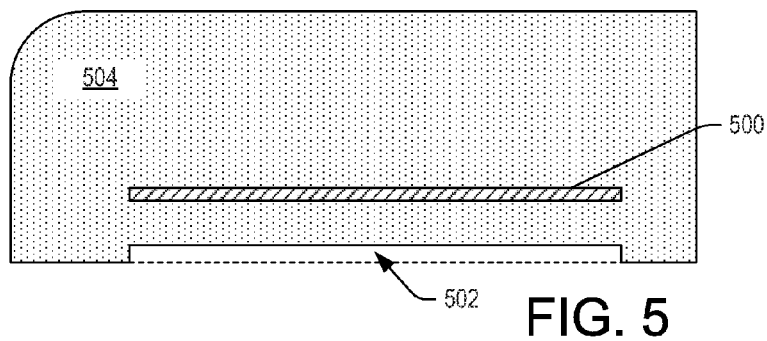
FIG. 5 depicts a cross-sectional view of an embodiment of a header with an antenna shield positioned in the header.

FIG. 5 depicts a cross-sectional view of an antenna shield 500 positioned in a header 504. The antenna shield 500 may be a solid conductive layer (e.g., a sheet of copper). In some embodiments, the antenna shield 500 may be coupled to the header 504 positioned in a recessed portion of the IMD so that the antenna shield 500 is positioned over at least a portion of an antenna coupled to a cover that substantially closes an opening in a housing of the IMD, is positioned over at least a portion of an antenna positioned within the housing of the IMD, or both. The antenna shield 500 may be positioned in the header 504, or may be coupled to the header 504. When the antenna shield 500 is coupled to the header 504, the antenna shield 500 may be coupled to, or deposited on, a bottom surface of the header 504; may be in the header; or may be coupled to a top surface of the header 504. When the antenna shield 500 is coupled to the top surface or the bottom surface of the header 504, the antenna shield 500 may be a biocompatible material or may be coated with a biocompatible material. In some embodiments, the antenna shield 500 may include one or more unshielded portions (e.g., one or more openings or one or more regions of non-conductive material interspersed in a region of conductive material).

The header 504 may be shaped to fit in a recessed portion of a housing of an IMD (e.g., the recessed portion 214 depicted in FIG. 4). The header 504 may include a recessed volume 502. The recessed volume 502 may accommodate a thickness of a seal, a cover (e.g., a ceramic sheet), and/or an antenna coupled to the cover that are sealed to a portion of the housing that defines an opening in the housing. In some embodiments, the cover may reside in a recess formed in a surface of the housing that accommodates the cover. In some embodiments, the cover may include a metal flange brazed, or otherwise attached to the outer perimeter of the cover. The metal flange may be configured to engage and be sealed to the edge of the housing defining the opening to close the opening. The flange may engage the opening from the inside or outside of the housing. Positioning the cover so that the flange engages the opening from the inside may allow the cover to be substantially flush with the surface of the recessed portion of the housing. Positioning the cover at least partially below the surface of the housing may reduce a needed depth of the recessed volume 502 when a seal for the cover, the cover, or both, extend above the surface. The recessed volume 502 may not be present when the seal for the cover and an upper surface of the cover are below or substantially flush with the housing.

When the antenna shield 500 is positioned in the header 504 over a planar antenna having one or more openings in a conductive layer of the antenna (such as the antenna 222 depicted in FIG. 3), the antenna shield 500 may extend over most or all of an area defined by the one or more openings in the conductive layer of the antenna. For example, the antenna shield 500 may extend over half of the area defined by the one or more openings, over 75% of the area defined by the one or more openings, or over all of the area defined by the one or more openings.

Various embodiments herein disclose implantable medical devices that include an antenna coupled to a cover that substantially closes an opening in a housing of the implantable medical device. The antenna may be a slot antenna or an antenna with another form factor. The antenna may be electrically coupled to the housing. Coupling the antenna to the housing may enable surfaces of the housing that form the opening to be radiating/receiving elements of the antenna. The antenna may include at least one feed feedthrough electrically coupled to a feed line of communication circuitry. The antenna may include one or more ground feedthroughs electrically coupled to a ground of the communication circuitry. The at least one feed feedthrough and the one or more ground feedthroughs may be electrically coupled to the antenna at locations that facilitate current flow associated with radio frequency signals at one or more communication frequencies along edges of a conductive layer of the antenna defined by a slot of the antenna. The antenna coupled to the cover may improve communication performance characteristics of the implantable medical device as compared to an implantable medical device with an antenna positioned within a housing of the implantable medical device. The antenna may also be coupled to a second antenna within the housing to further improve communication performance characteristics of the implantable medical device.

Figure 6:
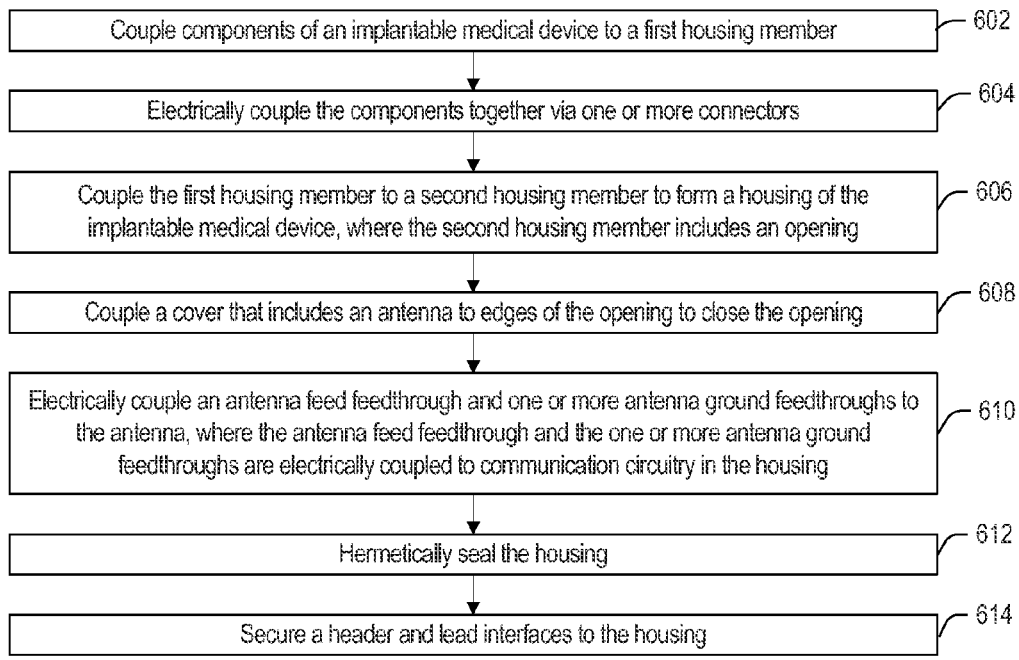
FIG. 6 depicts a flow chart of an embodiment of a method of manufacturing an implantable medical device.

FIG. 6 is a flow chart of a particular embodiment of a method of manufacturing an implantable medical device (IMD) with an antenna coupled to a cover for an opening in a housing of the IMD. The method may be performed to manufacture the IMD 102 of FIG. 1 or to manufacture the IMD 200 depicted in FIG. 2 with a header and lead interfaces. At 602, components of the IMD may be coupled to a first housing member. In some embodiments, one or more components may be coupled to a second housing member. The components may include a power source, functional circuitry (e.g., medical circuitry, a processor, a memory device, other components, or combinations thereof), communication circuitry, an output circuit board, or a combination thereof. In some embodiments, the output circuit board may include a second antenna. In other embodiments, the IMD may not include a second antenna within the housing of the IMD. One or more connectors may electrically couple the components together, at 604. The one or more connectors may include, but are not limited to circuit boards, wires, flexible connectors that attach to mating sockets, solder, or combinations thereof.

The output circuit board may include one or more lead interface feedthroughs that extend outwards from the circuit board. The lead interface feedthroughs may be electrically coupled to the medical circuitry. The output circuit board may also include an antenna feed feedthrough that extends outwards from the output circuit board and one or more antenna ground feedthroughs that extend outwards from the output circuit board. The antenna feed feedthrough and the one or more antenna ground feedthroughs may be electrically coupled to the communication circuitry. When the output circuit board includes the second antenna, the feed feedthrough, the ground feedthroughs, or both, may be electrically coupled to the second antenna.

A second housing member may be coupled to the first housing member to form the housing of the IMD, at 606. The second housing member may include an opening. The opening may be positioned above at least a portion of the output circuit board when the second member is coupled to the first member so that the one or more lead interface feedthroughs, the antenna feed feedthrough, and the one or more antenna ground feedthroughs extend through, or at least partially through, the opening in the second housing member. Positioners of the first housing member and the second housing member may guide proper alignment and positioning of the second housing member relative to the first housing member. The positioners may include pins, slots, grooves, keyways, or other elements that facilitate assembly, alignment, or both, of the first housing member relative to the second housing member. When the IMD includes the second antenna, one or more radiating/receiving elements of the second antenna may be positioned beneath the opening.

A cover that includes the antenna may be coupled to edges of the opening in the housing to substantially close the opening, at 608. The antenna may be a metal layer deposited, printed, adhered, or otherwise coupled to the cover. The cover may be a ceramic sheet. In some embodiments, the cover is coupled and sealed to the edges of the opening prior to coupling the first housing member to the second housing member. The cover and the antenna may include openings to accommodate the one or more lead interface feedthroughs, the antenna feed feedthrough, and the one or more antenna ground feedthroughs. In some embodiments, the antenna is electrically coupled to the second housing member. In some embodiments, the antenna is not electrically coupled to the second housing member when the cover is coupled to the second housing member.

The antenna feed feedthrough and the one or more antenna ground feedthroughs may be electrically coupled to the antenna, at 610. The antenna feed feedthrough and the one or more antenna ground feedthroughs may be electrically coupled to communication circuitry in the housing. When the IMD includes the second antenna, the antenna feed feedthrough, the one or more antenna ground feedthroughs, or both, may be electrically coupled to the second antenna.

The IMD may be hermetically sealed, at 612. Hermetically sealing the IMD may include sealing the first housing member to the second housing member (e.g., welding the first housing member to the second housing member), sealing the cover to the edges of the opening (e.g., brazing the cover to the edges of the opening), filling openings for the one or more lead interface feedthroughs with insulating sealant, sealing other openings in the housing, or combinations thereof.

A header and lead interfaces may be secured to the housing, at 614. The lead interfaces may be integral components of the header or separate components. The lead interfaces may be electrically coupled to the lead interface feedthroughs. In some embodiments, an antenna shield may be positioned above at least a portion of the antenna. The antenna shield may be coupled to the header. The antenna shield may be coupled to a top surface of the header, to a bottom surface of the header, or the antenna shield may be positioned in the header. The antenna shield may include one or more unshielded portions or may include no unshielded portions. In other embodiments, the IMD may not include an antenna shield.

Figure 7:
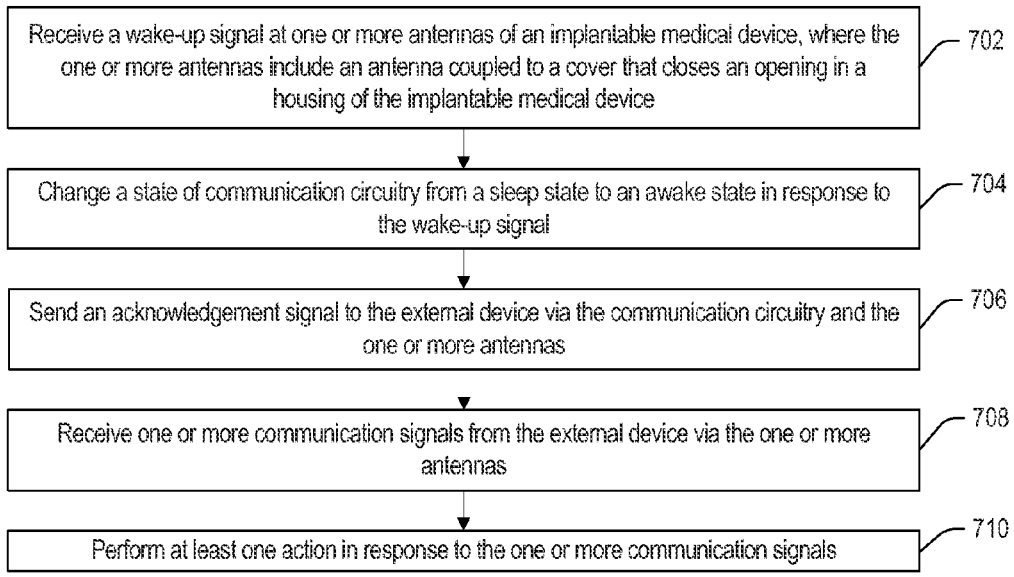
FIG. 7 depicts a flow chart of an embodiment of a method of communicating with an implantable medical device.

FIG. 7 is a flow chart of a particular embodiment of a method of communicating with an implantable medical device (IMD). The method may be performed by the IMD 102 of FIG. 1 and the IMD 200 of FIG. 2 (when the IMD 200 includes a header and lead interfaces; when the IMD 200 is coupled to one or more electrodes, one or more other devices, or both; and when the IMD 200 is implanted in a patient). An external device may send a wake-up signal to the IMD. At 702, the IMD may receive the wake-up signal at one or more antennas of the IMD. The one or more antennas may include an antenna coupled to a cover that substantially closes an opening in a housing of the implantable medical device.

The IMD may include components that are hermetically sealed within the housing. The components may include, but are not limited to, a power source, functional circuitry (e.g., medical circuitry, a processor, a memory device, other components, or combinations thereof), communication circuitry, wake-up circuitry, an output circuit board, and connectors. A portion of the output circuit board may be located beneath the opening in the housing that is sealed by the cover. In some embodiments, the output circuit board includes a second antenna of the one or more antennas. In some embodiments, an antenna shield may be positioned above all, or above portions, of the one or more antennas. The antenna shield may be coupled to a header that is secured (e.g., epoxied) to the housing. The antenna shield may improve the performance of the one or more antennas by attenuating low frequency signals received by the communication antenna (e.g., noise) to a greater extent than signals at communication frequencies (e.g., frequencies at or near 400 MHz) while still having relatively small attenuation due to the presence of the antenna shield at the communication frequencies.

In response to the wake-up signal, the IMD may change a state of communication circuitry from a sleep state, in which the communication circuitry is unpowered, to an awake state, in which power is supplied to the communication circuitry, at 704. The communication circuitry may be placed in the sleep state when the communication circuitry is inactive for a particular period of time or by a particular command received from the external device. When the communication circuitry is in the awake state, the communication circuitry may be able to receive first communication signals from the external device, may be able to send second communication signals to the external device, or both.

The IMD may send an acknowledgement signal to the external device via the communication circuitry and the one or more antennas, at 706. The acknowledgement signal may inform the external device that a communication session with the IMD is established.

The external device may send one or more communication signals to the IMD. The one or more communication signals may include commands for the IMD (e.g., requests for information, such as power source status, operation data, other information, or combinations thereof), may include operation instructions and operational data for the IMD (e.g., operation instructions and operation data that changes what treatment signals are sent by the IMD to the patient, when the treatment signals are sent to the patient, or both), other information, or combinations thereof.

The IMD may receive the one or more communication signals via the one or more antennas, at 708. The IMD may perform at least one action in response to the one or more communication signals, at 710.

Although the description above contains many specificities, these specificities illustrate some of the exemplary embodiments of this disclosure and should not be construed as limiting the scope of the disclosure. The scope of this disclosure should be determined by the claims, their legal equivalents and other embodiments which may become apparent to those skilled in the art. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. In the description, the terms "above," "below," and similar terms used in association with a structural element are used to denote relative positions or orientations associated with another structural element and with reference to the orientations depicted in the figures. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods and programs of the present disclosure. However, describing the disclosure with drawings should not be construed as imposing on the disclosure any limitations that may be present in the drawings. The present disclosure describes methods, systems and program products on any machine-readable media for accomplishing its operations. The embodiments of the present disclosure may be implemented using a computer processor, or by a special purpose computer processor incorporated for this or another purpose or by a hardwired system.

As noted above, embodiments within the scope of the present disclosure include program products comprising machine-readable media for carrying or having machine-executable instructions or data structures stored thereon. Such machine-readable media can be any available media which can be accessed by a general purpose or special purpose computer or other machine with a processor. By way of example, such machine-readable media can include RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media (e.g., a computer-readable storage device). Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

It should be noted that although the flowcharts provided herein show a specific order of method steps, it is understood that the order of these steps may differ from what is depicted. Also, two or more steps may be performed concurrently or with partial concurrence. It is understood that all such variations are within the scope of the disclosure. Likewise, software and web implementations of the present disclosure could be accomplished with standard programming techniques with rule based logic and other logic to accomplish the various steps. It should also be noted that the word "component" as used herein and in the claims is intended to encompass implementations using one or more lines of software code, and/or hardware implementations, and/or equipment for receiving manual inputs.

The foregoing description of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to a particular application.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. An implantable medical device comprising:
a housing having an opening;
communication circuitry in the housing;
a cover having an outside surface and an inside surface, the cover coupled to edges of the housing defining the opening to substantially close the opening;
an antenna on the outside surface of the cover, wherein the antenna is electrically coupled to the communication circuitry; and
a header coupled to the housing, wherein the cover is covered by the header.

2. The implantable medical device of claim 1, further comprising:
a feed feedthrough electrically coupled to the antenna from the communication circuitry; and
one or more ground feedthroughs electrically coupled to the antenna from the communication circuitry.

3. The implantable medical device of claim 1, wherein the cover comprises a dielectric material.

4. The implantable medical device of claim 1, wherein the antenna comprises a slot antenna.

5. The implantable medical device of claim 1, wherein the antenna is electrically coupled to the housing to enable at least one surface of the housing to be a radiating/receiving element of the antenna.

6. The implantable medical device of claim 1, further comprising an antenna shield coupled to the header.

7. The implantable medical device of claim 6, wherein the antenna shield is positioned over at least a portion of the antenna coupled to the outside surface of the cover.

8. The implantable medical device of claim 1, wherein the cover is coupled to the edges of the housing by an electrically conductive seal.

9. The implantable medical device of claim 8, wherein the electrically conductive seal comprises a metal flange coupled to an outer perimeter of the cover.

10. An implantable medical device comprising:
a housing having an opening;
communication circuitry in the housing;
a cover coupled to edges of the housing defining the opening to substantially close the opening;
a slot antenna coupled to the cover, wherein the slot antenna comprises a first conductive region proximate to a first side of a slot and a second conductive region proximate to a second side of the slot;
a feed feedthrough electrically coupled to the slot antenna adjacent to the slot in the first conductive region and electrically coupled to the communication circuitry; and
two or more ground feedthroughs electrically coupled to the slot antenna adjacent to the slot in the second conductive region and electrically coupled to the communication circuitry.

11. The implantable medical device of claim 10, wherein the two or more ground feedthroughs are coupled to a ground plane of a circuit board located below the opening.

12. The implantable medical device of claim 11, wherein the slot antenna is separated from the ground plane by a distance sufficient to inhibit capacitive coupling between the slot antenna and the ground plane.

13. The implantable medical device of claim 11 wherein the ground plane comprises a second slot antenna, wherein the second slot antenna is electrically coupled to the feed feedthrough.

14. The implantable medical device of claim 10, wherein the two or more ground feedthroughs are positioned relative to the feed feedthrough to promote current flow associated with radio frequency signals at one or more communication frequencies along edges of the slot antenna defined by the slot.

15. The implantable medical device of claim 10, wherein the cover has an outside surface and an inside surface, wherein the slot antenna is deposited on the outside surface of the cover.

16. The implantable medical device of claim 10, wherein the slot antenna is electrically coupled to the housing.

17. The implantable medical device of claim 10, wherein the feed feedthrough is proximate a centerline of the slot and the two or more ground feedthroughs are each offset from the centerline.

18. An implantable medical device comprising:
a housing having an opening;
a cover having an outside surface and an inside surface, the cover coupled to edges of the housing defining the opening to substantially close the opening, wherein the cover enables passage of radio frequency signals at one or more communication frequencies to and from a second antenna; and
a first antenna on the outside surface of the cover and electrically coupled to a circuit board in the housing;
wherein at least a portion of the circuit board is located below the opening, wherein the circuit board includes the second antenna, and wherein at least a portion of the second antenna is located below the opening.

19. The implantable medical device of claim 18, further comprising communication circuitry in the housing, wherein the first antenna and the second antenna are coupled to the communication circuitry.

20. The implantable medical device of claim 19, further comprising:
a feed feedthrough electrically coupled to the first antenna, and electrically coupled to the second antenna and the communication circuitry; and one or more ground feedthroughs electrically coupled to the first antenna, and electrically coupled to the second antenna and the communication circuitry.

21. The implantable medical device of claim 18, further comprising a header coupled to the housing, wherein the cover is covered by the header.

22. The implantable medical device of claim 18, wherein the first antenna is electrically coupled to the housing.

* * * * *